United States Patent [19]

Abegg et al.

[11] 4,011,878

[45] Mar. 15, 1977

[54] PROCESS FOR PERMANENTLY WAVING HAIR USING A SELF-HEATING NEUTRALIZING COMPOSITION CONTAINING A WATER-SOLUBLE SULFITE, METABISULFITE OR BISULFITE AND $H_2O_2$

[75] Inventors: Jean-Louis Abegg; Claire Gayet, both of Paris, France

[73] Assignee: Societe Anonyme dite: L'Oreal, Paris, France

[22] Filed: Nov. 29, 1974

[21] Appl. No.: 528,481

Related U.S. Application Data

[62] Division of Ser. No. 346,025, March 29, 1973, Pat. No. 3,865,930.

[30] Foreign Application Priority Data

Apr. 4, 1972 Luxembourg .......................... 65099

[52] U.S. Cl. .................................... 132/7; 424/71; 424/72
[51] Int. Cl.² ..................... A45D 7/06; A61K 7/09; A61K 7/11
[58] Field of Search .................... 132/7; 424/71, 72

[56] References Cited

UNITED STATES PATENTS 3,736,944   6/1973   Ghilardi et al. .................. 132/7

*Primary Examiner*—Sam Rosen
*Attorney, Agent, or Firm*—Cushman, Darby & Cushman

[57] ABSTRACT

A packaged, self-heating neutralizing composition for use in the second stage of a permanent waving operation comprises a first component selected from a water-soluble sulfite, bisulfite, metabisulfite or thiourea stored in one compartment of a two-compartment package and a second component comprising $H_2O_2$ separately stored in the second compartment of said two compartment package. Just before use, the said components are mixed together with an accompanying evolution of sensible heat. The resulting mixture contains free $H_2O_2$ in amounts of about 0.5–3 percent by weight of the composition.

4 Claims, No Drawings

PROCESS FOR PERMANENTLY WAVING HAIR USING A SELF-HEATING NEUTRALIZING COMPOSITION CONTAINING A WATER-SOLUBLE SULFITE, METABISULFITE OR BISULFITE AND $H_2O_2$

This is a division, of application Ser. No. 346,025, filed Mar. 29, 1973, now U.S. Pat. No. 3,865,930.

The present invention relates to self-heating neutralizing compositions for use in the second stage of a process for permanently waving hair and to a process for using these compositions.

It is known that a conventional method for permanently waving keratinic fibers, and particularly hair, consists in a first stage operation wherein the S—S linkages of the keratin fiber are opened, with the aid of a reducing agent such as a thiol, at an alkaline pH. Thereafter, the hair is preferably rinsed and subsequently treated in a second stage operation with an oxidizing or neutralizing agent to reconstitute the S—S bridges or linkages of the keratin so as to impart to the hair the desired configuration or style.

The present invention relates to a novel composition for use in this second stage of a permanent wave operation, which stage is often termed an "oxidation" or a "neutralization" operation wherein the S—S bridges of the keratin of the hair are re-formed. The novel compositions of the present invention exhibit the characteristics of being self-heating, i.e., they experience a temperature rise within a very short time after they have been prepared by mixing together the components from which they are formulated. This time period is generally a matter of a fraction of a minute up to about 1 to 2 minutes. The use of such self-heating or exothermic compositions to effect the second stage of a permanent wave operation provides not only the advantage that it produces a pleasing sensation on the head of the person undergoing the permanent wave operation due to the mild heating action of the composition but it also has the advantage that this temperature elevation accelerates the oxidation or neutralization reaction wherein the S—S bridges of the keratin are re-formed.

In one embodiment of the present invention there is provided a new product which constitutes a composition for use in the second stage of a permanent hair wave operation comprising a package having two separate storage means for separately storing the components of said composition and from which storage means said components are adapted to be dispensed for mixing with each other to provide said composition with the evolution of sensible heat, one of said storage means containing one of said components comprising a water soluble sulfite, metabisulfite or bisulfite, or thiourea and the other of said storage means containing another of said components comprising hydrogen peroxide, the said components being present in amounts such that the resulting mixture of said components (1) exhibits a rise in temperature of about 15°–25° C and (2) contains free $H_2O_2$ in amounts of about 0.5 to 3 percent by weight of said composition, and preferably in amounts of about 0.75–1.5 percent by weight of said composition.

The present invention also has for an object a composition for effecting the second stage of a process for permanently waving hair, comprising an aqueous solution of a first component comprising at least one compound selected from the group consisting of a water-soluble sulfite, metabisulfite or bisulfite and thiourea, and a second component comprising $H_2O_2$, the said components being present in amounts such that said mixture exhibits a rise in temperature of about 15°–25° C and contains free $H_2O_2$ in amounts of about 0.5–3 and preferably between 0.75–1.5 percent by weight of said mixture.

The present invention is also directed to a process for effecting the second phase or stage of a permanent wave operation of the hair in which the hair, after previously being reduced and rinsed is treated with a composition comprising a mixture of a first component comprising at least one compound selected from the group consisting of a water-soluble sulfite, metabisulfite, or bisulfite and thiourea and a second component comprising $H_2O_2$, the said components being present in amounts such that said mixture exhibits a rise in temperature of about 15° to 25° C and contains free $H_2O_2$ in amounts of about 0.5–3 and preferably between 0.75 and 1.5 percent by weight of said mixture.

According to one preferred embodiment of the invention, 100 grams of self-heating composition comprises a quantity of sulfite, bisulfite or metabisulfite sufficient to provide a concentration of 0.15–0.35 $SO_3^{--}$ group per 100 g of composition. When thiourea is employed it can be present in amounts of about 0.8–2 g per 100 g of said composition. It will be appreciated that as the content of sulfite, bisulfite, metabisulfite or thiourea is increased, there is a corresponding increase in the amount of temperature rise in the composition.

The concentration of $H_2O_2$ is a function, on the one hand, of the quantity of sulfite, bisulfite, metabisulfite or thiourea which is present in the composition, and on the other hand, of the concentration of free $H_2O_2$ that is desired in the composition at the end of the oxidation-reduction reaction.

The pH of the composition after mixture is generally between 0.5 and 7.

The present invention surprisingly demonstrates that the presence of the sulfite, bisulfite or metabisulfite, and more particularly the presence of thiourea, provides a temperature rise of about 15° to 25° C in a very rapid time, i.e., in about 1 to 2 minutes and that the elevated temperature obtained remains essentially constant at this elevated level for a period of time of about 10 to 15 minutes.

The rapid temperature rise to its maximum level provides the advantage that the composition can be used practically immediately after mixing together its component parts. This enables a significant savings in time and provides a simplified permanent waving operation, factors much sought after in beauty parlors.

The stability of the temperature of the composition is also an important factor, since it has been observed that in order to obtain good reconstitution of the S—S bridges of the keratin, it is generally necessary that the neutralizing agent effects the reconstitution in a period of about 5 to 15 minutes.

Representation water-soluble sulfites, metabisulfites and bisulfites, usefully employed in the present invention include the alkaline salts thereof such as sodium or potassium sulfite, sodium or potassium metabisulfite, sodium or potassium bisulfite as well as ammonium sulfite and the like.

According to one embodiment of the invention, the $H_2O_2$-containing component is stored in liquid form, to which has been added, if desired a conventional stabilizer.

The other component can be stored in the form of an aqueous solution or even in the form of a powder that can be dissolved, at the moment of use, in the $H_2O_2$-containing component.

According to the invention, the composition can also contain a thickening agent such as carboxymethyl cellulose, hydroxymethyl cellulose or a wax. Further the composition can also contain certain other conventional cosmetic adjuvants such as a perfume, dyes, stabilizers, preservatives, quaternary ammonium compounds, non-ionic compounds or anionic compounds. These adjuvants are preferably introduced into the liquid $H_2O_2$-containing component.

In accordance with the present invention, the reducing compound, i.e., the sulfite, bisulfite, metabisulfite or thiourea, preferably in the powder form, is dissolved rapidly and easily in the liquid $H_2O_2$-containing component.

To better understand the invention, the following non-limiting examples are given.

EXAMPLE 1

A package provided with two separate compartments contains in one compartment (Part A) 3 grams of anhydrous sodium sulfite. The other compartment contains 100 cc of $H_2O_2$ (9.8 volumes) — 2.94 weight % free $H_2O_2$, (Part B). The pH of part B is 2.7.

At the moment of use, part A is dissolved rapidly and without difficulty in part B.

The rate of temperature rise of the resulting mixture is as follows:

| Time: | | |
|---|---|---|
| | 0 min. | 20° C |
| | 1 min. | 39° C |
| | 2 min. | 40° C |
| | 3 min. | 39.5° C |
| | 4 min. | 39° C |
| | 5 min. | 38.5° C |
| | 6 min. | 38° C |
| | 10 min. | 36.5° C |
| | 15 min. | 35° C |

The final composition is a solution of $H_2O_2$ — 7.1 volumes, containing 2.13 g of free $H_2O_2$, having a pH of 3.

EXAMPLE 2

A package similar to that of Example 1, houses in one compartment:
Part A
Sodium metabisulfite — 2.25 g and in the other compartment:
Part B
100 cc of $H_2O_2$ solution — 9.8 volumes (2.94 weight percent free $H_2O_2$)
The pH of part B is 2.7.

Just prior to use, part A and part B are mixed together, the dissolution being rapid and being exothermic.

The rate of temperature rise of the resulting mixture is as follows:

| Time: | | |
|---|---|---|
| | 0 min. | 20° C |
| | 1 min. | 37° C |
| | 2 min. | 38° C |
| | 3 min. | 37.5° C |
| | 4 min. | 37° C |
| | 5 min. | 37° C |
| | 6 min. | 36.5° C |
| | 10 min. | 35° C |
| | 15 min. | 34° C |

The final composition is a solution of $H_2O_2$ — 7 volumes (2.1 weight percent solution of free $H_2O_2$).

EXAMPLE 3

A package similar to that of Example 1, houses in one compartment.
Part A
Thiourea — 1.3 g
and in the other compartment:

| Part B | |
|---|---|
| Phenacetin | 0.1 g |
| Citric acid | 0.1 g |
| $H_2O_2$, q.s.p. 10 volumes (3 weight percent free $H_2O_2$) | |
| Dye | 0.2 g |
| Water, q.s.p. | 100 cc |
| The pH of part B is 2.3. | |

At the moment of use, part A is mixed and rapidly dissolved in part B, the dissolution being exothermic.

The rate of temperature rise in the resulting mixture is as follows:

| Time: | | |
|---|---|---|
| | 0 min. | 20° C |
| | 1 min. | 36° C |
| | 2 min. | 39° C |
| | 3 min. | 39° C |
| | 4 min. | 38.5° C |
| | 5 min. | 38° C |
| | 6 min. | 38° C |
| | 10 min. | 37° C |
| | 15 min. | 35° C |

The final composition is a solution of $H_2O_2$ — 7.4 volumes (2.22 weight percent of free $H_2O_2$), having a pH of 1.7.

EXAMPLE 4

After having reduced hair rolled on permanent hair waving rollers with the following composition:

| After having reduced hair rolled on permanent hair waving rollers with the following composition: | |
|---|---|
| Thioglycolic acid | 8 g |
| Ammonia, q.s.p. neutralization | |
| Monoethanolamine | 4.5 g |
| Dye | 0.2 g |
| Perfume | 0.1 g |
| Water, q.s.p. | 100 cc, | the hair is thoroughly rinsed with water. To the thus rinsed hair there is applied a composition of the present invention resulting from mixing of the below described parts A and B:

Part A (housed in a first compartment of a two-compartment package)
Anhydrous sodium sulfite — 3 g
Part B (housed in a second compartment of the said two compartment package)

| Part B (housed in a second compartment of the said two compartment package) |
|---|
| Cire de Sipol (mixture of 30% cetyl |

| | |
|---|---|
| alcohol and 70% stearyl alcohol oxyethylenated with 33 moles of ethylene oxide per mol of alcohol) | 0.75 g |
| Cetyltrimethyl ammonium bromide | 0.10 g |
| Phenacetin | 0.10 g |
| Hydroxy quinoline sulfate of the formula | |

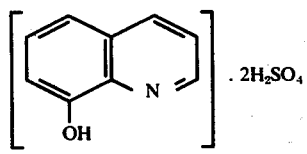

| | |
|---|---|
| Citric acid | 0.12 g |
| H₂O₂, q.s.p. 8 volumes (2.4 weight percent free H₂O₂) | |
| Perfume | 0.05 g |
| Dye | 0.12 g |
| Water, q.s.p. | 100 cc |

The pH of part B is 3.4.

Part A and part B are mixed together, the resulting mixture exhibiting a pH of 3.4 and having a concentration of free $H_2O_2$ of 1.5 weight percent (5 volumes).

The initial temperature of the mixture is, of course, essentially ambient temperature but after about 60 to 90 seconds, the internal temperature rises to about 38° C. The composition is then applied to the hair wound on conventional rollers where it reacts to re-build the disulfide bridges of the keratin of the hair for about 5 to 10 minutes.

After removing the rollers and rinsing the hair, the hair exhibits an excellent curl.

Essentially identical results are achieved when sodium sulfite in the above composition is replaced with potassium sulfite.

EXAMPLE 5

After having effected the first stage, i.e., a reducing stage to break the disulfide linkages of the keratin in a permanent waving operation using the following reducing composition:

| | |
|---|---|
| Thioglycolic acid | 7 g |
| Ammonium sesquicarbonate | 11 g |
| Sweet almond oil | 0.2 g |
| Perfume | 0.1 g |
| Dye | 0.15 g |
| Water, q.s.p. | 100 cc | the hair is rinsed thoroughly with water. Thereafter the thus rinsed hair, in the second "oxidation" or "neutralization" stage, is contacted with a composition according to the present invention resulting from mixing part A and part B, as follows:

Part A (housed in a first compartment of a two compartment package)

Anhydrous sodium sulfite — 3 g

| | |
|---|---|
| Part B (housed in a second compartment of said two compartment package) | |
| Cetyltrimethylammonium bromide | 0.7 g |
| Phenacetin | 0.05 g |
| Phosphoric acid | 0.1 g |
| Galactomanose 80% - Water 20% - Sold under the tradename Guarante AL 90 | 1 g |
| H₂O₂, q.s.p. 10 volumes (3 weight percent free H₂O₂) | |
| Water, q.s.p. | 100 cc |

The pH of part B is 2.4.

The resulting mixture of parts A and B exhibits a pH of 3 and has a concentration of $H_2O_2$ of 7 volumes (2.1 weight percent free $H_2O_2$).

After 60–95 seconds, the internal temperature of the composition rises from essentially ambient temperature to about 41° C, at which time the composition is applied to the hair wound on conventional curlers where it reacts for about 10–15 minutes to re-form the disulfide linkages of the keratin. The rollers are then removed and the hair is thoroughly rinsed with water, thus providing a permanent of excellent quality.

EXAMPLE 6

After having effected the first stage of a permanent waving operation as indicated in Example 5, the hair is rinsed and to the thus rinsed hair there is applied the composition of the invention resulting from mixing 50 cc of part A and 50 cc of part B, as follows, part A and part B being separately stored in a first and second compartment, respectively, of a two compartment package.

Part A

Aqueous solution of ammonium sulfite 5.52 g/100 cc

Part B

Solution of $H_2O_2$ — 17.9 volumes (5.36 weight percent free $H_2O_2$)

pH = 2.1.

The composition resulting from the mixture of parts A and B exhibits a pH of 2.3 and has a concentration of free $H_2O_2$ of 1.86 weight percent (6.2 volumes).

After 30–90 seconds, the internal temperature of the composition rises from essentially ambient temperature to about 39° C at which time the composition is applied to the hair wound on conventional curlers where it reacts for a period of about 5–10 minutes to re-build the disulfide linkages of the keratin. The rollers are then removed and the hair is thoroughly rinsed with water thus providing a permanent of excellent quality.

EXAMPLE 7

Example 6 is repeated except that the composition for the second stage of the permanent waving operation is replaced by a composition resulting from the mixture of 50 cc of part A and 50 cc of part B as follows:

Part A

Aqueous solution of sodium bisulfite 4.94 g/100 cc

Part B

Solution of $H_2O_2$ — 17.9 volumes (5.36 weight percent free $H_2O_2$)

pH = 2.1.

After mixture, the resulting composition exhibits a pH of 0.9 and has a concentration of free $H_2O_2$ of 1.95 weight percent (6.5 volumes).

The rate of temperature rise in the resulting mixture is as follows:

| Time: | | |
|---|---|---|
| | 0 min. | 20° C |
| | 1 min. | 37° C |
| | 2 min. | 37° C |
| | 3 min. | 36.5° C |
| | 4 min. | 36° C |
| | 5 min. | 35° C |
| | 6 min. | 35° C |

| | |
|---|---|
| 10 min. | 34° C |
| 15 min. | 32° C |

The composition is applied to the hair after about 30 to 60 seconds. Permanents exhibiting excellent curl and holding power are also obtained when in Examples 4 and 5, the composition according to the invention is replaced by one of the compositions described in Examples 1, 2 or 3.

Excellent permanents are also obtained when sodium sulfite and sodium metabisulfite of Examples 1 and 2, respectively, are replaced by potassium sulfite or metabisulfite.

What is claimed is:

1. A process for effecting the second stage of a permanent wave operation of the hair, said hair previously having been reduced, rinsed and wound on rollers, comprising the steps of treating said hair for a period of about 5 to 15 minutes with a composition consisting essentially of a mixture of a first component comprising a water-soluble salt selected from the group consisting of sodium, potassium and ammonium sulfite; sodium, potassium and ammonium metabisulfite; and sodium, potassium and ammonium bisulfite; and a second component comprising $H_2O_2$, the said components being present in amounts such that the said mixture exhibits a temperature rise of about 15° to 25° C and contains free $H_2O_2$ in amounts of about 0.5–3 percent by weight of said composition, removing said rollers and rinsing said hair.

2. The process of claim 1 wherein said composition has a pH between about 0.5 and 7.

3. The process of claim 1 wherein said composition contains free $H_2O_2$ in amounts of about 0.75–1.5 percent by weight of said composition.

4. A process for effecting the second stage of a permanent wave operation of the hair, said hair previously having been reduced, rinsed and wound on rollers, comprising the steps of treating said hair for a period of about 5 to 15 minutes with a composition consisting essentially of a mixture of a first component comprising a water soluble salt selected from the group consisting of sodium, potassium and ammonium sulfite; sodium, potassium and ammonium metabisulfite; and sodium, potassium and ammonium bisulfite; and a second component comprising $H_2O_2$, the said components being present in amounts such that the said mixture exhibits a temperature rise of about 15° to 25° C within a period ranging from a fraction of a minute to 2 minutes with the resulting elevated temperature remaining constant for a period of about 10–15 minutes and such that the said mixture contains free $H_2O_2$ in amounts of about 0.5–3 percent by weight of said composition, removing said rollers and rinsing said hair.

* * * * *